(12) United States Patent
Luks et al.

(10) Patent No.: US 12,059,213 B2
(45) Date of Patent: *Aug. 13, 2024

(54) INTERACTIVE DISPLAY FOR SURGERY WITH MOTHER AND DAUGHTER VIDEO FEEDS

(71) Applicant: University Surgical Associates, Inc., Rumford, RI (US)

(72) Inventors: Francois I. Luks, Barrington, RI (US); Derek Merck, Barrington, RI (US)

(73) Assignee: University Surgical Associates, Inc., Rumford, RI (US)

( * ) Notice: Subject to any disclaimer, the term of this patent is extended or adjusted under 35 U.S.C. 154(b) by 680 days.

This patent is subject to a terminal disclaimer.

(21) Appl. No.: 17/244,390

(22) Filed: Apr. 29, 2021

(65) Prior Publication Data
US 2021/0244486 A1    Aug. 12, 2021

Related U.S. Application Data

(63) Continuation of application No. 16/673,185, filed on Nov. 4, 2019, now Pat. No. 11,051,890, which is a (Continued)

(51) Int. Cl.
A61B 1/00    (2006.01)
A61B 1/045    (2006.01)
(Continued)

(52) U.S. Cl.
CPC ........ A61B 34/20 (2016.02); A61B 1/000095 (2022.02); A61B 1/00011 (2013.01);
(Continued)

(58) Field of Classification Search
CPC . A61B 34/20; A61B 1/00009; A61B 1/00011; A61B 1/00045; A61B 1/0005;
(Continued)

(56) References Cited

U.S. PATENT DOCUMENTS

| 5,397,323 A | 3/1995 | Taylor et al. |
| 5,657,429 A | 8/1997 | Wang et al. |

(Continued)

FOREIGN PATENT DOCUMENTS

EP    0655710 A2    5/1995

OTHER PUBLICATIONS

Aidlen et al. (Aug. 2009) "Head-Motion-Controlled Video Goggles: Preliminary Concept for an Interactive Laparoscopic Image Display (i-LID)", Journal of Laparoendoscopic & Advanced Surgical Techniques, 19(4):595-598.

(Continued)

Primary Examiner — Timothy J Neal
Assistant Examiner — William B Chou
(74) Attorney, Agent, or Firm — Mintz Levin Cohn Ferris Glovsky and Popeo, P.C.

(57) ABSTRACT

Data characterizing a mother video feed acquired by an endoscopic video capture device can be received. The mother video feed can be for characterizing an operative field within a patient. One or more predefined markers can be identified within the mother video feed. Each of the one or more predefined markers can be associated with a surgical instrument in the operative field. Using the data characterizing the mother video feed, a daughter video feed comprising a sub-portion of the mother video feed can be generated. At least one of a location of the daughter video feed within the mother video feed and a zoom of the daughter video feed can be based on the identified one or more predefined markers. The daughter video feed can be provided. Related apparatus, systems, techniques, and articles are also described.

20 Claims, 11 Drawing Sheets

Related U.S. Application Data continuation of application No. 15/121,670, filed as application No. PCT/US2015/018081 on Feb. 27, 2015, now Pat. No. 10,499,994.

(60) Provisional application No. 61/945,673, filed on Feb. 27, 2014.

(51) Int. Cl.
*A61B 1/313* (2006.01)
*A61B 34/20* (2016.01)

(52) U.S. Cl.
CPC ........ *A61B 1/00045* (2013.01); *A61B 1/0005* (2013.01); *A61B 1/00188* (2013.01); *A61B 1/045* (2013.01); *A61B 1/3132* (2013.01); *A61B 2034/2055* (2016.02); *A61B 2034/2074* (2016.02)

(58) Field of Classification Search
CPC .... A61B 1/00188; A61B 1/045; A61B 1/3132
See application file for complete search history.

(56) References Cited

U.S. PATENT DOCUMENTS

| | | |
|---|---|---|
| 5,820,545 A | 10/1998 | Arbter et al. |
| 5,836,869 A | 11/1998 | Kudo et al. |
| 5,907,664 A | 5/1999 | Wang et al. |
| 6,434,416 B1 | 8/2002 | Mizoguchi et al. |
| 6,436,107 B1 | 8/2002 | Wang et al. |
| 6,463,361 B1 | 10/2002 | Wang et al. |
| 6,553,281 B1 | 4/2003 | Liu |
| 6,636,254 B1 | 10/2003 | Onishi et al. |
| 6,659,939 B2 | 12/2003 | Moll et al. |
| 7,087,049 B2 | 8/2006 | Nowlin et al. |
| 7,491,165 B2 | 2/2009 | Kogasaka et al. |
| 7,686,451 B2 | 3/2010 | Cleveland |
| 8,108,072 B2 | 1/2012 | Zhao et al. |
| 8,187,167 B2 | 5/2012 | Kim |
| 8,199,188 B2 | 6/2012 | Amling et al. |
| 8,248,414 B2 | 8/2012 | Gattani et al. |
| 8,313,432 B2 | 11/2012 | Chiu et al. |
| 8,504,136 B1 | 8/2013 | Sun et al. |
| 8,527,094 B2 | 9/2013 | Kumar et al. |
| 10,499,994 B2 | 12/2019 | Luks et al. |
| 11,051,890 B2 | 7/2021 | Luks et al. |
| 2003/0053202 A1 | 3/2003 | Sibata et al. |
| 2005/0033580 A1 | 2/2005 | Wang et al. |
| 2006/0071135 A1 | 4/2006 | Trovato |
| 2007/0197865 A1 | 8/2007 | Miyake et al. |
| 2008/0262297 A1 | 10/2008 | Gilboa et al. |
| 2009/0074265 A1 | 3/2009 | Huang et al. |
| 2009/0199125 A1 | 8/2009 | Sekiguchi et al. |
| 2009/0248041 A1 | 10/2009 | Williams et al. |
| 2010/0111389 A1 | 5/2010 | Strobel et al. |
| 2012/0062717 A1 | 3/2012 | Kinouchi et al. |
| 2012/0071752 A1 | 3/2012 | Sewell et al. |
| 2013/0245375 A1* | 9/2013 | DiMaio ............... A61B 34/30 600/166 |
| 2013/0331644 A1 | 12/2013 | Pandya et al. |
| 2014/0049626 A1 | 2/2014 | Ishihara |
| 2015/0077528 A1 | 3/2015 | Awdeh |
| 2015/0138329 A1 | 5/2015 | Braun et al. |
| 2017/0027650 A1 | 2/2017 | Merck et al. |
| 2017/0046833 A1 | 2/2017 | Lurie et al. |
| 2018/0324414 A1 | 11/2018 | Hoffman et al. |
| 2020/0078099 A1 | 3/2020 | Luks et al. |

OTHER PUBLICATIONS

Avra Medical Robotics Inc (2017) "Surgical Robots", All About Robotics Surgery, The Official Medical Robotics News Center Sponsored by AVRA Medical Robotics Inc.

Cuschieri et al. (Apr. 2006) "Epistemology of Visual Imaging in Endoscopic Surgery", Surgical Endoscopy and Other Interventional Techniques, 20(Suppl 2):S419-S424.

Erfanian et al. (Jul. 2003) "In-line Image Projection Accelerates Task Performance in Laparoscopic Appendectomy", Journal of Pediatric Surgery, 38(7):1059-1062.

Eto et al., "Robotic Surgery Assisted by the ZEUS System", Department of Urology, Graduate School of Medical Sciences, Kyushu University, 3-1-1 Maidashi, Higashi-ku, Fukuoka 812-8582, Japan, 10 pages.

Forgione (Apr. 2-5, 2014) "A Novel, Image Based, Active Laparoscope Manipulator—Preliminary Clinical Results with the AutoLap system", Presented at the Annual Conference of the Society of American Gastrointestinal and Endoscopic Surgeons (SAGES), 1 page (Abstract only).

Heemskerk et al. (May 2006) "Advantages of Advanced Laparoscopic Systems", Surgical Endoscopy and Other Interventional Techniques, 20(5):730-733.

Intuitive Surgical, Inc, "da Vinci Surgical System", Intuitive Surgical, Inc. Apr. 2009, https://intuitivesurgical.com/products/davinci_surgical_system/davinci_surgical_system_si/, 1 page.

King et al. (Dec. 9, 2013) "Towards an Autonomous Robot for Camera Control During Laparoscopic Surgery", Journal of Laparoendoscopic & Advanced Surgical Techniques, 23(12):1027-1030.

Kumar et al. (Mar. 2014) "Stereoscopic Visualization of Laparoscope Image Using Depth Information from 3D Model", Computer Methods and Programs in Biomedicine, 113(3):862-868.

Luks et al. (Apr. 2-5, 2014) "i-LID—Instrument-driven Laparoscopic Image Display", Presented at the Annual Conference of the Society of American Gastrointestinal and Endoscopic Surgeons (SAGES), 1 page (Abstract Only).

Muratore et al. (Jun. 2007) "Image Display in Endoscopic Surgery", Journal of the Society for Information Display, 15(6):349-356.

Nister et al. (Jun. 2004) "An Efficient Solution to the Five-Point Relative Pose Problem", IEEE Transactions on Pattern Analysis and Machine Intelligence, 26(6):756-770.

Peters et al. (Jan. 2004) "Development and Validation of a Comprehensive Program of Education and Assessment of the Basic Fundamentals of Laparoscopic Surgery", Surgery, SAGES FLS Committee, 135(1):21-27.

Prendergast et al. (Nov. 2008) "Surgical Performance with Head-Mounted Displays in Laparoscopic Surgery", Journal of Laparoendoscopic & Advanced Surgical Techniques, 19(S1):S237-S240.

Sony Corporation (Jul. 23, 2013) "Sony Introduces 'head-mount image processing unit' for endoscopic image display", Sony Corporation, https://www.sony.net/SonyInfo/News/Press/201307/13-085E/, 7 pages.

Spaner et al. (Dec. 1997) "A Brief History of Endoscopy, Laparoscopy, and Laparoscopic Surgery", Journal of Laparoendoscopic & Advanced Surgical Techniques, 7(6):369-373.

Stellato et al. (Oct. 1992) "History of Laparoscopic Surgery", Surgical Clinics of North America, 72(5):997-1002.

Te Velde et al. (Jan. 2008) "Minimally Invasive Pediatric Surgery: Increasing Implementation in Daily Practice and Resident's Training", Surgical Endoscopy, 22(1):163-166.

Thakkar et al. (Dec. 2012) "Individualized Image Display Improves Performance in Laparoscopic Surgery", Journal of Laparoendoscopic & Advanced Surgical Techniques, 22(10):1010-1013.

Tokunaga (Jan. 2014) "Improving Performance under Mirror-Image Conditions during Laparoscopic Surgery using the Broadview Camera System", Asian Journal of Endoscopic Surgery, 7(1):17-24.

Virtual Medical Worlds (Jun. 2, 2000) "Computer Motion to start patent infringement war on medical robotics against Intuitive Surgical", Virtual Medical Worlds, http://www.hoise.com/vmw/00/articles/vmw/LV-VM-07-00-18.html, 2 pages.

Wilhelm et al. (Aug. 2014) "Comparative Evaluation of HD 2D/3D Laparoscopic Monitors and Benchmarking to a Theoretically Ideal 3D Pseudodisplay: Even well-Experienced Laparoscopists Perform Better with 3D", Surgical Endoscopy, 28(8):2387-2397.

\* cited by examiner

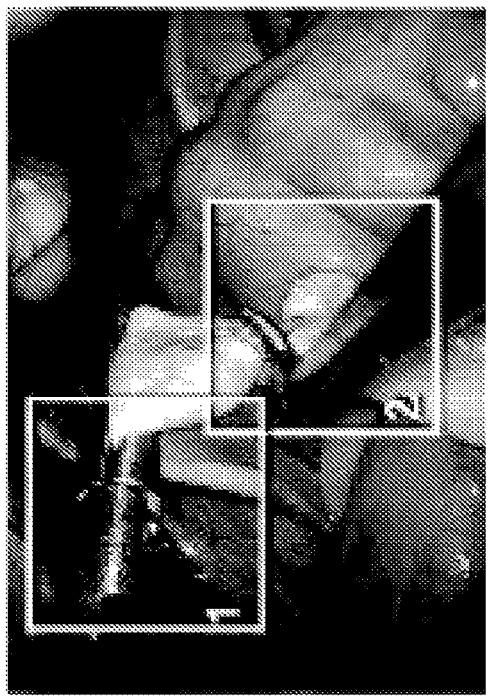
FIG. 6

INTERACTIVE DISPLAY FOR SURGERY WITH MOTHER AND DAUGHTER VIDEO FEEDS

CROSS-REFERENCE TO RELATED APPLICATIONS

This application is a continuation and claims the benefit and priority under 35 U.S.C § 120 to U.S. application Ser. No. 16/673,185 filed Nov. 4, 2019, which is a continuation and claims the benefit and priority under 35 U.S.C § 120 to U.S. application Ser. No. 15/121,670 filed Aug. 25 2016, and granted as U.S. Pat. No. 10,499,994, which is a national stage application filed under 35 U.S.C. 371, of International Patent Application No. PCT/US15/18081 filed Feb. 27, 2015 and claims priority to U.S. Provisional Application No. 61/945,673 filed Feb. 27, 2014, the entire contents of which is hereby expressly incorporated by reference herein.

TECHNICAL FIELD

The subject matter described herein relates to providing multiple interactive views of a captured video feed. The video feed can be captured during surgery such as laparoscopy and other forms of minimally invasive or videoscopic procedures.

BACKGROUND

Laparoscopic surgery and other forms of minimally invasive surgery (MIS) procedures include a large proportion of surgical interventions in the United States. Techniques have greatly improved since the late 1980s, but the goal of emulating traditional (e.g., open) surgery has not been reached. Instrumentation has been miniaturized, image quality has been increased, and the addition of robotics promises to compensate for human limitations. Yet there is a limitation of MIS: unlike open surgery, the operative field is dependent on a single viewpoint provided by the telescope and camera, and every member of the surgical team sees the same image. The consequences are that a) the displayed image depends entirely on the view captured by the cameraman (e.g., the person holding the telescope and camera), who can be subject to fatigue, tremor, or poor instructions from the surgeon, resulting in suboptimal capture (and therefore display) of the operative field; b) tunnel vision (e.g., a risk of blind spots and unseen injuries if the telescope and camera shows a zoomed-in image of the surgical field); c) the image can be a panoramic view of the surgical field, which shows a wide angle—but removes any detail, or a close-up, which creates tunnel vision—but not both; and d) there can only be one surgical action at any given time.

At best, this set-up prevents multitasking, simultaneous performance of multiple maneuvers and observation of the field from several points of view (all features of open surgery); at worst, it offers a suboptimal view of the field and endangers the patient by omitting critical parts of the operative field. As a result, and despite its overall safety, laparoscopic operations are still not as safe as their traditional, open counterparts.

SUMMARY

In an aspect, data characterizing a mother video feed acquired by an endoscopic video capture device can be received. The mother video feed can be for characterizing an operative field within a patient. One or more predefined markers can be identified within the mother video feed. Each of the one or more predefined markers can be associated with a surgical instrument in the operative field. Using the data characterizing the mother video feed, a daughter video feed comprising a sub-portion of the mother video feed can be generated. At least one of a location of the daughter video feed within the mother video feed and a zoom of the daughter video feed can be based on the identified one or more predefined markers. The daughter video feed can be provided.

One or more of the following features can be included in any feasible combination. For example, the one or more predefined markers can be tracked through the mother video feed. The daughter video feed location can be centered on one of the identified one or more predefined markers. The generated daughter video feed can automatically pan through the mother video feed by changing the location of the daughter video feed and based on the tracking of the one or more predefined markers. The generated daughter video feed can automatically change the level of magnification within the mother video feed by changing the zoom of the daughter video feed and based on the tracking of the one or more predefined markers. Each of the one or more predefined markers can be located at or near a distal end of the associated surgical instrument.

The endoscopic video capture device can be hand-held. The location of the daughter video feed can define a sub-portion of the mother video feed. The zoom of the daughter video feed can define a level of magnification and a window size. The location of the daughter video feed within the mother video feed can be based on a location of one of the identified one or more predefined markers. The zoom of the daughter video feed can be based on a present size of one of the identified one or more predefined markers within the mother video feed.

Using the mother video feed, a second daughter video feed comprising a second sub-portion of the mother video feed can be generated. At least one of a location of the second daughter video feed within the mother video feed and a zoom of the second daughter video feed can be based on the identified one or more predefined markers. The second daughter video feed can be provided. Providing can include at least one of displaying, transmitting, storing, or processing. Providing can include displaying the daughter video feed and the second daughter video feed separately for viewing during videoscopic procedures. The sub-portion of the mother video feed can be a windowed portion of the mother video feed. The location and the zoom of the daughter video feed can be independent of a position and/or a gaze of a surgeon.

Computer program products are also described that comprise non-transitory computer readable media storing instructions, which when executed by at least one data processor of one or more computing systems, cause at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The subject matter described herein can provide many advantages. For example, the current subject matter can allow each surgeon or member of an operating team or holder of an endoscopic instrument to determine what portion of the operative field to observe on the monitor or screen. Each surgeon or member of the operating team or holder of an endoscopic instrument can determine which degree of detail (e.g., zoom) to view. Each daughter video feed can be centered, or otherwise framed, windowed, or cropped around each operator's instrument, thereby becoming independent of the framing or centering of a mother video feed, which can reduce or even eliminate unwanted image motion (such as tremor, drift and other image imperfections), which may be introduced by inexperienced or poor camera manipulation. By offering multiple daughter views of the field, multiple tasks can be performed at the same time, even if they are occurring in different parts of the operating field (e.g., multi-tasking). By offering multiple simultaneous degrees of zooming, close-up and panoramic views of the field can occur at the same time, reducing blind spot/tunnel vision while maintaining sufficient detail of the operating field. By utilizing an instrument as an image navigating tool, hands-free, intuitive manipulation of the image (including panning, zooming and other actions) can occur.

In some implementations, the current subject matter allows for a reduced number of ports, which can also reduce the number of hands needed during an operation. For example the camera may use a port utilized by a surgical instrument. In some implementations, multiple cameras can be used to allow seamless transitions from camera to camera and their various angles. In some implementations, the point of view can change as a surgeon moves around an operating table, allowing the surgeon to determine their optimal viewing point, regardless of their position at the operating table. The current subject matter allows for tracking of multiple independent views of the operative field, each view controlled by a different operator (via their respective instrument), and without the need for multiple cameras or moving cameras. In some implementations, multiple cameras can be used to create the mother image and/or to create multiple mother images, each having daughter images.

The current subject matter can also provide for multitasking, e.g., surgeons can focus on more than one aspect of an operation at the same time. For example, teachers can look at the big picture (or other portions of the field) while the trainee focuses on an aspect of the operation; or conversely, the teacher can optimize his/her view, regardless of where the assistant is looking. As another example, there can be simultaneous zoomed-in and panoramic views: one surgeon zooms in on a delicate task requiring extreme close-up and magnification, while another surgeon looks at a wider view, to ensure injuries at a distance do not occur).

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 6 is a series of photographs illustrating an example mother video feed (left) with two daughter video feeds (right);

Like reference symbols in the various drawings indicate like elements.

DETAILED DESCRIPTION

Figure 1:
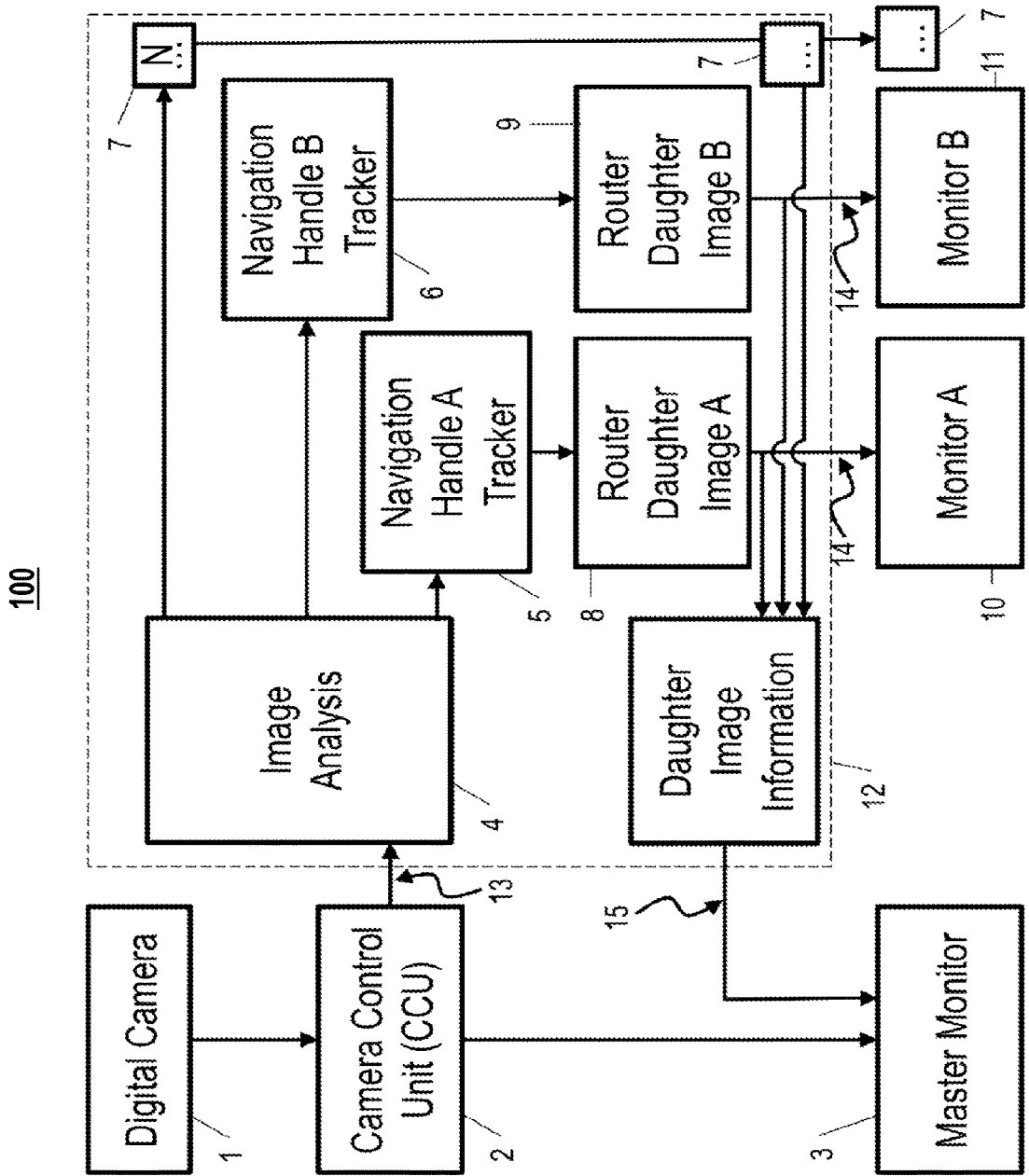
FIG. 1 is a system block diagram of a system illustrating an example implementation according to the current subject matter.

An example implementation of the subject matter described herein includes a supplementary device that provides a display with multiple and different daughter video feeds of a mother video feed at the same time. The mother video feed can be a video captured during laparoscopic or other videoscopic procedures. A daughter video feed is a sub-image or sub-portion of the mother video feed, such as a windowed/cropped or zoomed-in portion of the mother video feed. The device allows different users to independently pan and zoom each daughter based on a separate endoscopic instrument using specific markers or characteristics of, or on, that instrument (e.g., including, but not limited to, color or combination of colors, patterns, shape, electronic signal and the like) and without moving the camera generating the mother video feed. Thus, multiple daughter video feeds can be generated from a single mother video feed, with each daughter video feed being independently manipulated by the position of the marker on an instrument (e.g., its tip). In this manner, multiple surgeons can gain independent "views" of the operative field at the same time using a single camera and/or video feed. In addition, regardless of the quality of the image capture, there is automatic negation of tremor, camera drift, and other imperfections of image capture.

In some example implementations, image capture technology (e.g., High Definition (HD) image technology) allows electronic zooming of a portion of the daughter video feed without pixilation. In some implementations, one or more of cropping, panning, zooming and other manipulation of a video image can be driven by a combination of external parameters, input or devices, such as toggle switch, joystick, foot pedal and the like, and/or driven by a characteristic within the captured image itself, such as a specific pattern, color, combination of colors, shape or other image detail. A software-driven implementation can assign a role of navigating handle to a specific characteristic of the image, localized at or near the working portion of an endoscopic instrument (for example, a color, combination of colors, pattern or shape), and frame a close-up daughter video feed of the captured mother video feed around this navigating handle. Software can track the position of this navigating handle in real time, forcing the daughter video feed to track its position (e.g., by automatically panning, zooming, and the like, through the mother video feed). Further details of the navigating handle, including (but not limited to) relative size of the patterns, allows the tracking software to distinguish the distance of the instrument relative to the camera and thus dictate the degree of close-up (zoom) of the "daughter" image, so that the software not only tracks the navigating handle in an X and Y axis (e.g., plane perpendicular to the axis camera-target) but in the Z axis as well (e.g., degree of zooming toward the target).

In some example implementations, an unlimited number of independent daughter video feeds can be constructed and independently tracked, as an unlimited variety of characteristics (such as colors, combinations of colors, patterns, shapes or electronic signals) can be used on an unlimited number of endoscopic instruments. Each daughter video feed can be displayed on a separate monitor or screen, so that each instrument holder (surgeon/member of the operating team) can view a dedicated monitor or screen with its unique, independently manipulated daughter video feed.

FIG. 1 is a system block diagram of a system 100 illustrating an example implementation according to the current subject matter. A set-up for laparoscopy and other videoscopic procedures can include a digital charge-coupled device (CCD) camera 1 or other imaging device, mounted on a telescope, and connected to a camera control unit (CCU) 2. The CCU 2 interfaces with a master monitor 3, and one or more additional video monitors, screens, or other video image display devices 10, 11, 7. In some implementations, the digital camera captures a wide view of the entire operating field. In some implementations, the digital camera can be held by hand and is not steered by a motor or other actuator. A supplemental device 12 can receive image data via a video interface 13. Image analysis software 14 can be included that can identify predefined markers within a mother video feed captured by the digital camera 1, such as colors, patterns, combinations of colors, electronic signals or any other unique characteristic. Each unique marker, or navigation handle, can be tracked by a navigation handle tracker 5, 6, 7. There can be any number of unique navigation handles A, B, each with their own dedicated navigation handle tracker 5, 6. Each of the navigation handle trackers 5, 6, can instruct a respective router 8, 9, to window, frame, or crop a respective unique daughter video feed. Navigation handle A can steer navigation handle A tracker 5, navigation handle B steers navigation handle B tracker 6, and so on 7. Using information from each navigation handle tracker 5, 6, routers 8, 9, can pan, zoom in/out, frame or otherwise manipulate a portion of the mother video feed into independently moving daughter video feeds. Navigation handle A tracker 5 can instruct Router 8 into projecting daughter video feed A onto Monitor 10, navigation handle B tracker 6 can instructs Router 9 into projecting daughter video feed B onto monitor 11, and so on 7. Output interface of the device 12 can be any format of image/video data transmission 14, including SDI, RGB, S-video, and the like. In addition, the information from each router 8, 9, can be displayed onto at least one Master monitor 3 as well, via any form of interface 15.

Figure 2:
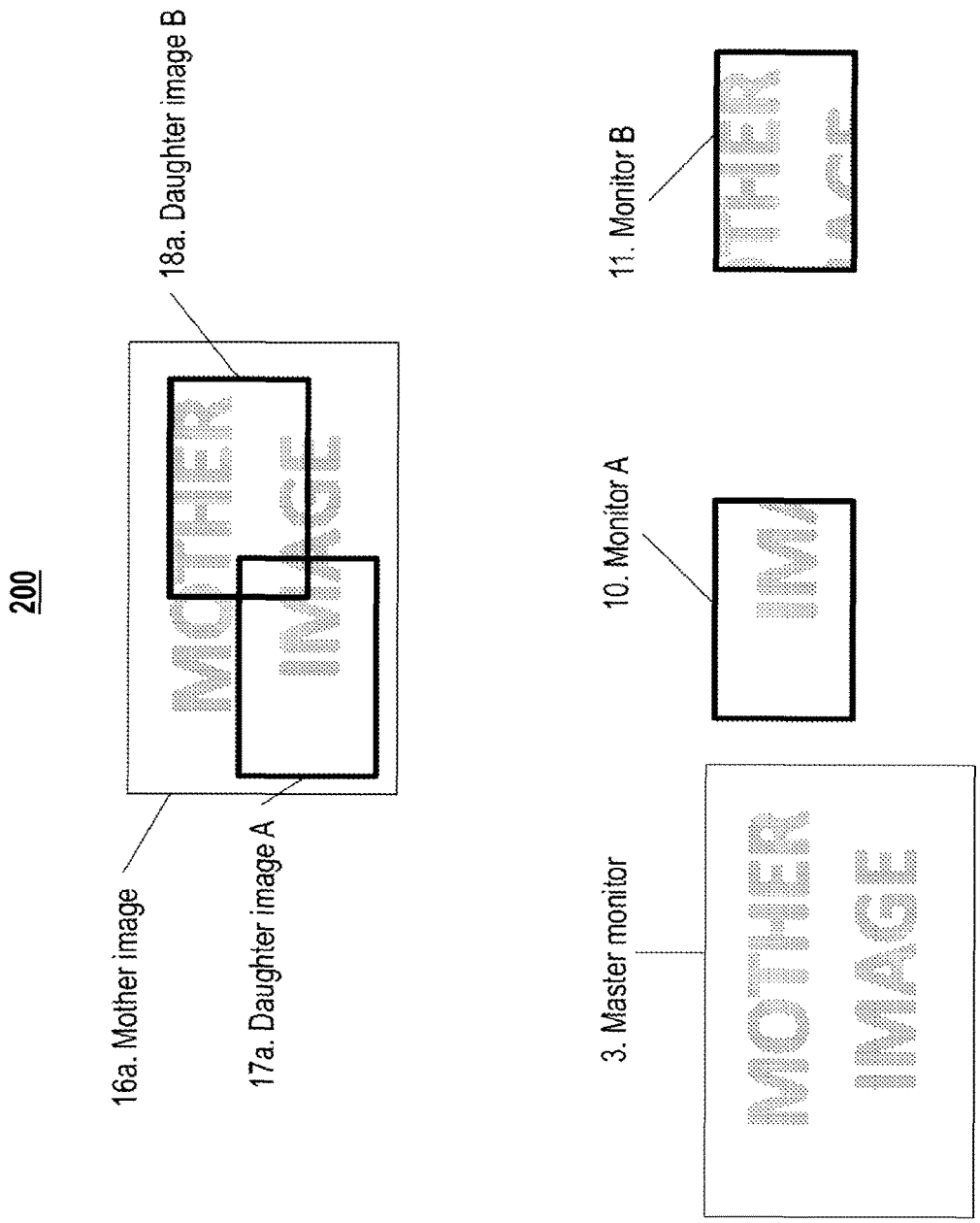
FIG. 2 is a schematic example illustrating the relationship between example mother and daughter video feeds.

FIG. 2 is a schematic example 200 illustrating the relationship between example mother and daughter video feeds. An image captured by an endoscopic video camera comprises a Mother video feed 16a, which can be a high definition image with a ratio of 1920×1080 pixels. From this mother video feed 16a, any number of predefined and independently moveable (pan, zoom, etc.) daughter video feeds 17a, 18a, can be defined (in the example of FIG. 2, daughter video feed A 17a and daughter video feed B 18a are illustrated). The entire mother video feed 17a can be displayed on one or more Master monitors 3. In addition, each daughter video feed 17a, 18a, can be displayed on at least one dedicated monitor 10, 11. In the example of FIG. 2, daughter video feed A 17a is displayed on Monitor A 10 and daughter video feed B 18a is displayed on Monitor B 11.

Figure 3:
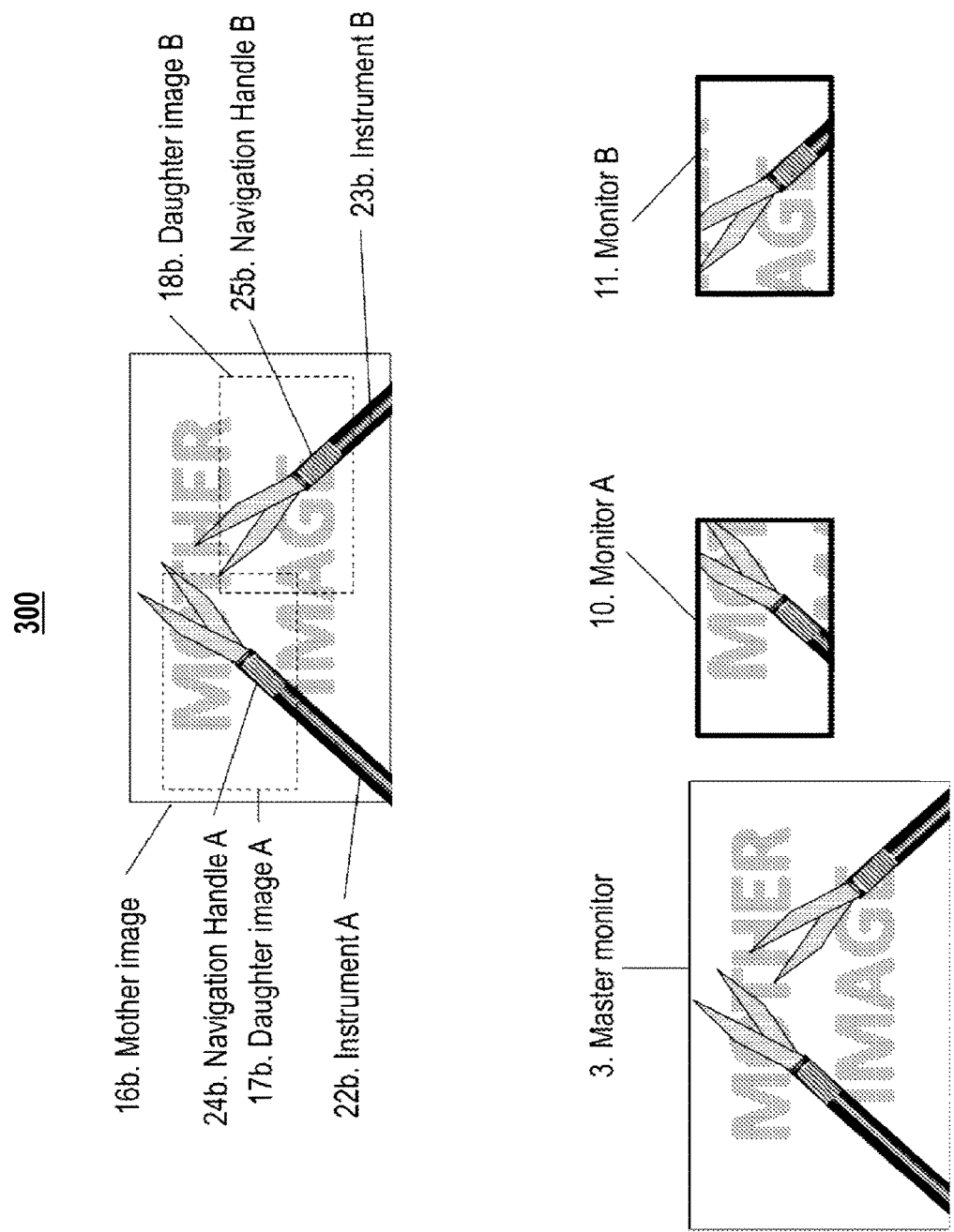
FIG. 3 is a schematic example illustrating panning navigation of daughter video feeds.

FIG. 3 is a schematic example 300 illustrating panning navigation of daughter video feeds. Any number of predefined markers (colors, combinations colors, patterns, electronic signal or any other specific characteristic within the mother video feed) can be used to manipulate daughter video feeds. In the example illustrated in FIG. 3, endoscopic instrument A 22b contains a marker, or navigation handle, near its active tip, consisting of longitudinal parallel lines 24b, while endoscopic instrument B 23b contains a navigation handle consisting of transverse parallel lines 25b. Each daughter video feed, which is a portion of the mother video feed 16b is centered around its dedicated navigation handle. Daughter video feed A 17b is centered around Navigation handle A 24b, while daughter video feed B 18b is centered around Navigation handle B 25b. The entire mother video feed 16b, including a view on both instruments in this example, can be displayed on at least one Master monitor 3. In addition, each daughter video feed can be displayed onto at least one dedicated monitor (e.g., Monitor A 10 for daughter video feed A 17a, Monitor B 11 for daughter video feed B 18b in this example).

Figure 4:
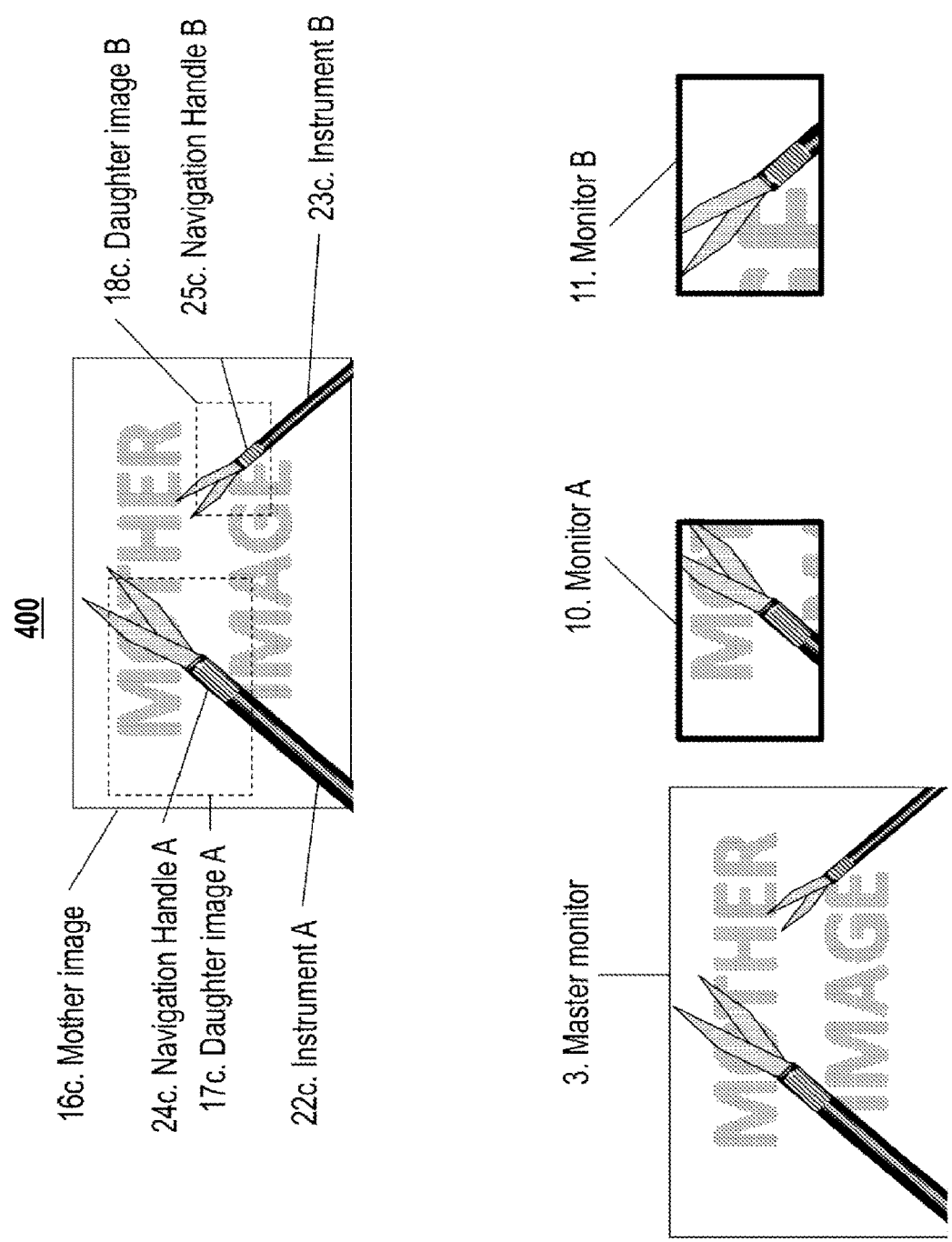
FIG. 4 is a schematic example illustrating various degrees of zooming of daughter video feeds.

FIG. 4 is a schematic example 400 illustrating zooming navigation of daughter video feeds. The daughter video feeds in FIG. 4 have zoomed, panned, or otherwise moved to other locations on the mother video feed.

Zooming navigation of daughter video feeds can occur. A shape, pattern, color, combination of colors, electronic signal, or any changing perception of a navigation handle can determine a degree of close-up (zoom) of a daughter video feed. In the example of FIG. 4, instrument A 22c is relatively close to the camera, as seen in the mother video feed 16c. The relative position, size, or other characteristics of its navigation handle A 24c can determine the degree of zooming of daughter video feed A 17c (e.g., the size of the window relative to the size of the mother video feed), which is displayed onto monitor A 10. Instrument B 23c appears further away from the camera (and therefore appears smaller). The relative position, size, or other characteristics of its navigation handle B 25c can therefore be different than for instrument A and, in this example, this difference within navigation handle B 25c can determine a greater close-up of daughter video feed B 18c. Master monitor 3 displays the entire captured image, including—in this example—the two endoscopic instruments. Monitor A 10 displays daughter video feed A 17c, while monitor B 11 displays daughter video feed B 18c in greater close-up than daughter video feed A.

During an operation, a surgeon wishing to change their viewpoint can manipulate a daughter video feed by manipulating an instrument. The camera 1 does not need to be moved (either automatically for example, by a motor or other control device, or manually, for example, by a member of the surgical team). From the perspective of the surgical team, it can appear that each instrument has a dedicated camera that automatically pans and zooms based on movement of the instrument. Using the current subject matter, this can be achieved with a single camera 1.

Figure 5:
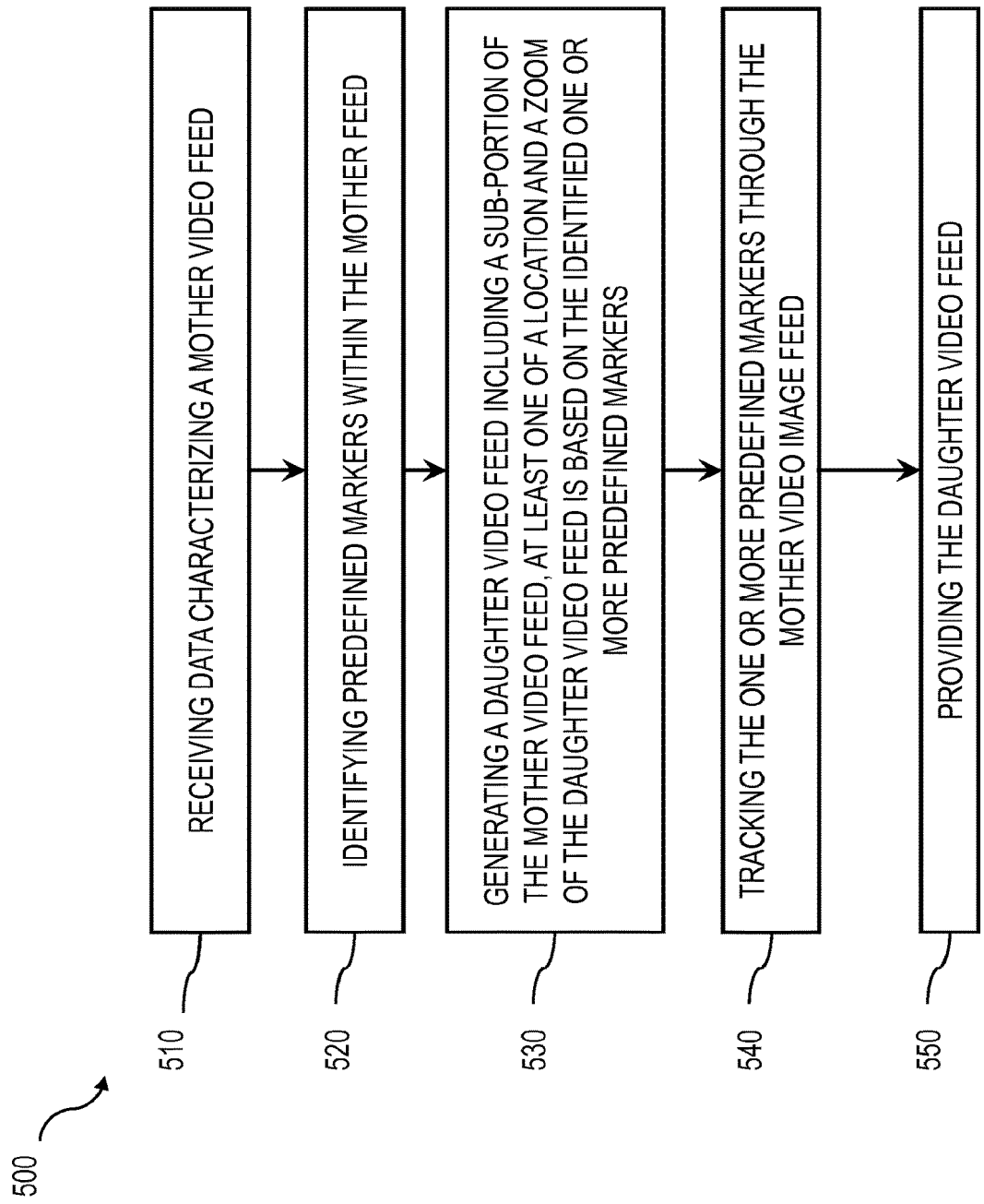
FIG. 5 is a process flow diagram of a method for generating daughter video feeds.

FIG. 5 is a process flow diagram 500 of a method for generating daughter video feeds. These daughter video feeds can each be centered on a tip or working portion of a surgical instrument and can be manipulated by the position of the instrument's working portion without having to move a camera (e.g., an endoscopic video capture device can be static such that it is not required to move in order for the daughter video feeds to track the surgical instruments). Surgical instruments can include any device or instrument intended for use during a videoscopic procedure.

Data can be received at 510 characterizing a mother video feed. The mother video feed can be acquired by an endoscopic video capture device, such as an endoscopic camera used a videoscopic procedure. The mother video feed can be of an operative field within a patient (e.g., can be taken during surgery for characterizing the operative field).

The mother video image can be generated by a high-resolution camera (e.g., camera 1). While there is no standardized meaning for high-definition or high-resolution, generally any video image with more than 480 horizontal lines (North America) or 576 lines (Europe) is considered high-definition. 720 scan lines is generally the minimum even though the majority of systems greatly exceed that. Images of standard resolution captured at rates faster than normal (60 frames/second North America, 50 fps Europe), by a high-speed camera may be considered high-definition in some contexts.

One or more predefined markers within the mother video feed can be identified at 520. The one or more predefined markers can be associated with a surgical instrument in the operative field. For example, the predefined markers can be located at or near a distal end or working portion of an associated surgical instrument. The surgical instrument can be an endoscopic instrument. The one or more predefined markers can include one or more of colors, patterns, combinations of colors, electronic signals, and the like.

A daughter video feed comprising a sub-portion of the mother video feed can be generated at 530 using the data characterizing the mother video feed. The sub-portion of the mother video feed can be a windowed portion of the mother video feed. At least one of a location and zoom of the daughter video feed can be based on the identified one or more predefined markers. The location of the daughter video feed can define the window (e.g., sub-portion) within the mother video feed that comprises the daughter video feed. The zoom of the daughter video feed can define the resolution and/or size of the window; a smaller sized window causes the daughter video feed to appear "zoomed in" while a larger sized window causes the daughter video feed to appear "zoomed out." The resolution of the daughter video feed can also change based on the level of zoom. In addition, the location and zoom of the daughter video feed can be independent of a position and/or gaze of a surgeon.

The location of the daughter video feed can be based on a present location of the associated predefined markers (in an X and Y plane perpendicular to the axis of camera-target). The daughter video feed can be centered on the predefined marker or localized so as to keep the predefined marker within a predefined zone.

The zoom of the daughter video feed can be based on a present size of the associated predefined marker. The size of the associated predefined marker can characterize a distance or depth of the predefined marker from the camera (in the Z axis).

In some implementations, one or more additional daughter video feeds can be generated. The additional daughter video feeds can be second sub-portions of the mother video feed. The additional daughter video feeds can have a location and zoom based off associated identified predefined markers.

In some example implementations, at 540, the one or more predefined markers can be tracked between mother video feed video frames. The location and zoom of the daughter video feed can be updated based on the tracking of the predefined markers.

At 550, the daughter video feed can be provided. Providing can include displaying, transmitting, storing, or processing the daughter video feed. Providing can include displaying the daughter video feed for viewing during videoscopic procedures. The additional daughter video feeds can also be provided.

The generated daughter video feed can automatically pan through the mother video feed by changing the location of the daughter video feed (e.g., as the instrument moves) and based on tracking the predefined markers. The daughter video feed can also automatically change frame size within the mother video feed by changing the zoom of the daughter video feed (so that the window size increases or decreases giving the appearance of zooming in or out). This magnification change and zooming can be based on the tracking of the predefined markers.

In some implementations, multiple cameras or a fish-eye camera can be used. The daughter video feed can seamlessly transition from camera to camera and their various angles, for example, based on whether the predefined marker is within a field of view of the camera. In other words, if the predefined marker leaves a first mother image but is within a second mother image, the daughter image can switch from the first mother image to the second mother image. In addition, the point of view can change as the surgeon moves around the operating table. A concern of MIS is paradoxical imaging, where the surgeon faces the camera, rather than being in line with it, causes motions to be viewed in opposite directions on the monitor (e.g., motions to the left appear to the right on the screen, moving away from the surgeon appears as moving toward the screen, and the like). With multiple cameras and/or ports, each surgeon can determine their optimal viewpoint, regardless of their position at the operating table.

In some implementations, daughter video feeds can be post-processed using image/video processing techniques. For example, the daughter video feeds can have any shaking artefacts from a user holding the camera removed, the images can be enhanced, and the like.

First Example Implementation

Laparoscopy and other forms of minimally invasive ("key-hole") surgery (MIS) comprise a large proportion of surgical interventions in the United States. Techniques have greatly improved since the late 1980s, but there is one limitation of MIS that has never been addressed: unlike traditional, open surgery, the operative field is entirely dependent on a single viewpoint provided by the telescope/camera, and every member of the surgical team sees the same image. This set-up eliminates peripheral vision of the operative field and places every member of the team at the mercy of the cameraman. At worst, critical aspects of the operative field may be missed entirely or the image may drift or shake, particularly when the camera is in the hands of a less experienced member of the team. At best, this single viewpoint is either a wide-angle image, which results in a loss of detail; or a close-up, which causes loss of peripheral vision and endangers the patient by omitting critical parts of the operative field. As a result, and despite its overall benefits, laparoscopic operations are still not as safe as their traditional, open counter-parts. A widely publicized reminder of this occurred when John Murtha (senior member of the U.S. Congress) underwent a routine laparoscopic gallbladder removal at one of the nation's premier hospitals in February 2010—and died a week later from complications of an unrecognized bowel injury—precisely because of the tunnel vision effect of current laparoscopy.

Unfortunately, this is hardly an isolated incident. The high mortality rate from bowel injuries (16-18%) is a medicolegal finding that is proper to laparoscopic cholecystectomies (and one that was virtually unheard of with open surgery). The incidence of other complications, such as bile duct injuries, remains 2-4 times higher after laparoscopy than after open cholecystectomy. The "cost" to these patients is enormous, and a bile duct injury increases the risk of death after laparoscopic cholecystectomy 2.7-2.8 times, regardless of patient age. Even when the laparoscopic image is optimal, the absence of multiple simultaneous views prevents multitasking (a common occurrence in open surgery). This contributes to longer operative times for most types of laparoscopic procedures.

Providing each member of the surgical team with an individualized, instrument-driven, optimal view of the operative field significantly improves the capabilities of minimally invasive surgery. The current subject matter can A) reduce operative time, as various steps of a surgical maneuver can be performed simultaneously, and B) enhance surgical accuracy, as close-ups and peripheral vision coexist.

A goal is to develop a stand-alone, platform-independent device that can be inserted between the endoscopic image capture device and the image displays. The advantages of such supplemental technology are 1) independence from any specific brand of endoscopic system, allowing widespread application without the need to overhaul an entire endoscopic operating room, 2) coexistence of the device with standard endoscopic image display, facilitating its acceptance and guaranteeing patient safety, and 3) limited patient safety concerns, as the device will not be in contact with the patient or disrupt image capture-to-display stream—thereby easing regulatory procedures for its use in an operating room setting.

Figure 7:
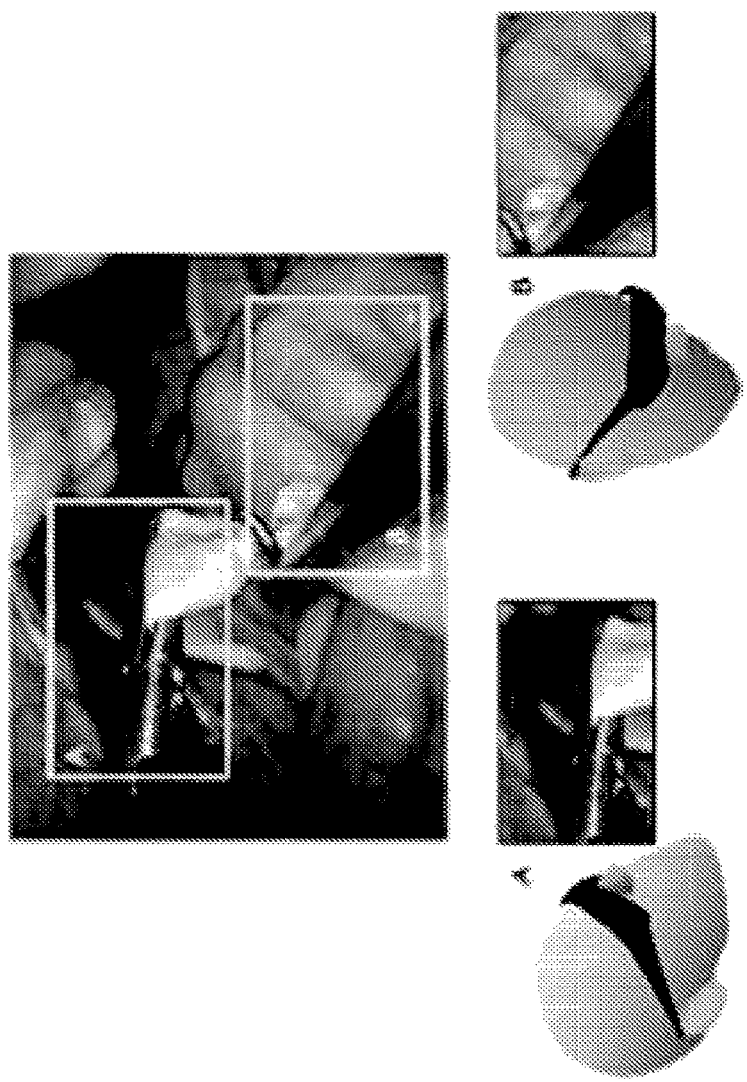
FIG. 7 is a series of photographs illustrating the example mother and daughter video feeds of FIG. 6 being displayed in a headset.

Example aspects can include 1) the freedom of multiple, simultaneous image viewpoints, which until now was reserved for open surgery; 2) the ability to graft this new technology onto existing infrastructure; and 3) designation of the surgical instrument as the primary determinant of image navigation. This provides an intuitive, always-centered image that is not only independent from another team member's view, but independent from image capture errors: even if the (often novice) camera operator fails to steady or center the "mother" image, the individual "daughter" images are determined by where the individual surgeons want it to be (that is, centered on their primary instrument). While some examples utilize two independent image trackers, the same can be expanded to any numbers of tracking instruments and/or operators. Of course, "opt-out" switch (i.e., return to the "mother" image), alternating between left-hand and right-hand instruments as the tracking point and image stabilization can all be features included. The juxtaposition of various existing components (High-Definition video output, surgical instruments and video image displays) with customized software navigation and a plug-in hardware component will have the ability to turn any operating room into a multi-image, enhanced MIS suite without the need for major overhaul. This "plug-and-play" supplemental device will allow wide-spread distribution: the number of MIS operations performed each year in the United States alone is estimated at more than 7 million. FIG. 7 Manipulation of the HMD video image by spatial recognition of the surgeon's gaze: as surgeon looks up (a=A), image pans up; as surgeon looks down (B), image pans down.

While HMDs epitomize image individualization and maximize hand-eye coordination by keeping the target image and the operator's instruments in the same field of vision, they have limited practical use. Immersion technology isolates the operator from collaborators, which may impair critical communication and interaction during surgical interventions. Profile designs restrict environment awareness and peripheral vision, which may be dangerous for surgeons. Until robust wireless technology is available, they tether the surgeon to the operating table, and this nuisance becomes a hazard if multiple team members are likewise tethered by cables. Safety is also compromised if the surgeon cannot quickly switch from HMD to a standard monitor in case of emergency (or HMD malfunction). Furthermore, inner ear-, balance- and even nausea problems have been described with poorly synchronized head motion and image projection through HMD. Finally, wide acceptance of a new interactive imaging system might be hampered by the need to switch to expensive, and initially disorienting HMD.

Although overhead video monitors offer more environment awareness than HMDs, the simultaneous display of independently moving images could theoretically cause confusion, and be less, rather than more, efficient. The feasibility and value of a multi-user multiple display system in a validated in vitro model of MIS. Two-surgeon exercises were performed with a single camera (control), and with two surgeon-controlled cameras, each generating a separate image. A significant reduction in operating time, for two different exercises, is possible with the use of individual cameras. Moreover, the reduction in operative time can be more pronounced in the expert group than in the novice group. This indicates that the device is not just a tool to help shorten the learning curve for new users (assuming that experts will adapt to any system, even an imperfect one). Rather, it offers the advanced laparoscopists access to skills they were previously unable to perform—multitasking and simultaneously focusing on a close-up of the target and on a wider operative field.

Figure 8:
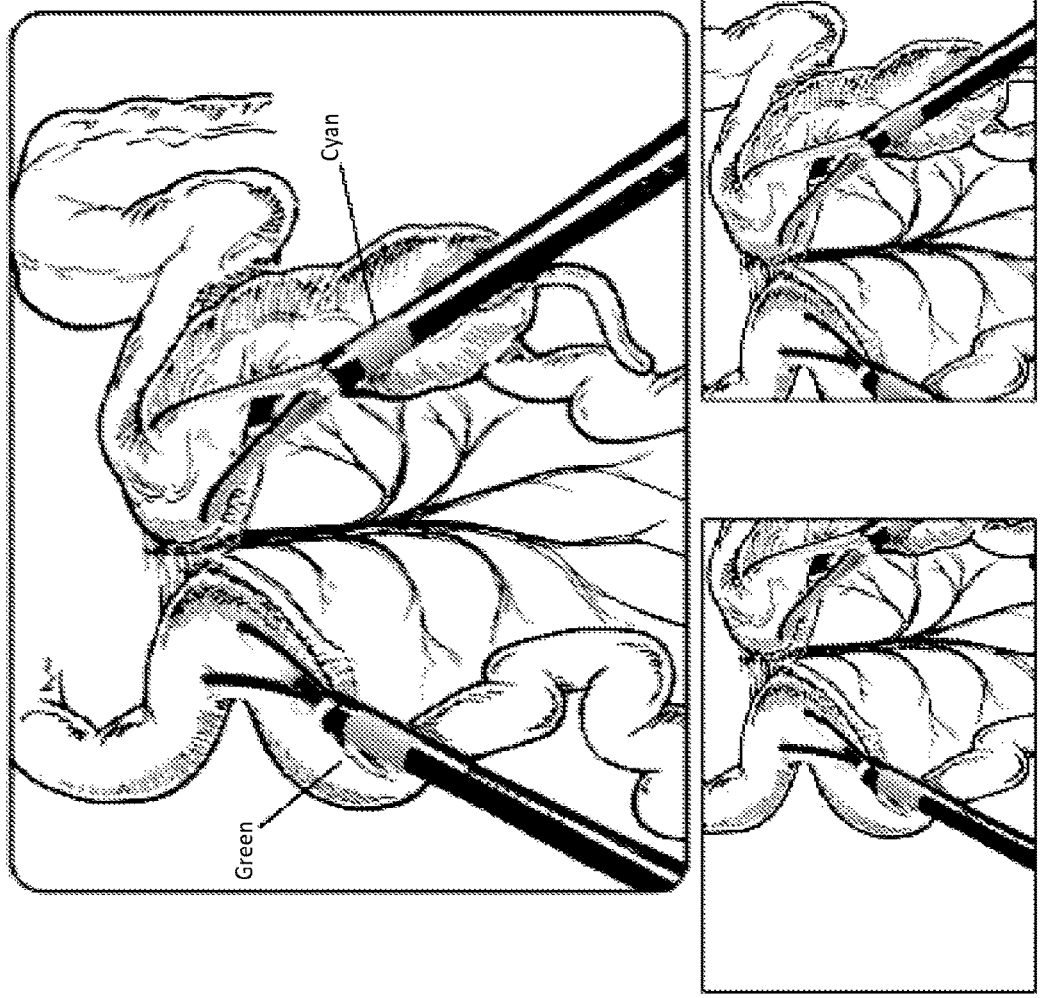
FIG. 8 is an illustration of how manipulation of a daughter video feed location (e.g., window) can be triggered by the recognition of a unique color reference (mounted as a ring of colored tape close to the tip of an endoscopic instrument)

A software-based navigation system can allow panning and zooming of a "daughter" window within a "mother" image. Manipulation of a window can be triggered by the recognition of a unique color reference (mounted as a ring of colored tape close to the tip of an endoscopic instrument) (FIG. 8).

In some examples, the input video stream can come from a USB camera device for the initial design. A video capture device connected to a standard endoscope and light source can be utilized to simulate future clinical application. An arbitrary number of instrument/window pairs can be supported, up to the limits of acceptable latency. A set of straightforward distinct hue targets can be used in some implementations, supporting up to four simultaneous instrument/viewports for yellow-, green-, cyan-, and pink-coded instruments. Daughter windows can be spread across multiple displays arranged to suit individual operators.

Image processing/display pipeline can include these steps: 1. Master image is collected from the video stream. 2. For each window: Camera image is thresholded for optical targets (distinct hues in the simplest case); Thresholded image moments are computed and instrument tip image position is estimated based on known instrument geometry; A depth estimate is made; For distinct hues, depth estimation is based on the relative size of the visible target (e.g. smaller=further away); Tip position estimate is input into a Kalman filter to smooth the estimate over time, and an improved estimate is generated; Original image is cropped and scaled for rendering in the daughter window; Cropping is about the tip, scaling may be manually controlled, or driven by a dynamic depth estimate (e.g. farther away=zoom in). If a global navigation view is being used, the master image is annotated with extents and targets for each daughter viewport and various parameters such as frames per second and task time are rendered in a separate window.

Preferably latency can be below 50-100 ms, similar to the latency observed in a standard clinical endoscopic camera and display. The system can be multithreaded and pipelined to minimize latency.

The display router can include a desktop computer with high-end video processing system capable of providing simultaneous display of up to 4 daughter windows with minimal latency (defined as 50-80 ms for the purpose of in vitro testing); input capabilities for a USB camera or DVI and SDI interface with a standard HD camera control unit; and VGA, SDI and DVI output capabilities.

Second Example Implementation

A significant limitation of minimally invasive surgery (MIS) can be dependence of the entire surgical team on a single endoscopic viewpoint. An individualized, instrument-driven image display system that allows all operators to simultaneously define their viewing frame of the surgical field may be the solution. Tested is the efficacy of such a system using a modified Fundamentals of Laparoscopic Surgery (FLS®) bead transfer task.

Methods: A program was custom-written to allow zooming and centering of the image window on specific color signals, each attached near the tip of a different laparoscopic instrument. Two controls were used for the bead transfer task: 1) static, wide-angle view, and 2) single moving camera allowing close-up and tracking of the bead as it was transferred. Time to task completion and number of bead drops were recorded.

Results: Thirty-six sessions were performed by surgical residents. Average time for bead transfer was 127.3±21.3 s in the Experimental group, 139.1±27.8 s in Control 1 and 186.2±18.5 s in Control 2 (P=0.034, ANOVA). Paired analysis (Wilcoxon Signed Rank Test) showed that the Experimental group was significantly faster than the Control 1 group (P=0.035) and the Control 2 group (P=0.028).

Conclusions: Developed is an image navigation system that allows intuitive and efficient laparoscopic performance compared with two controls. It offers high resolution images and ability for multi-tasking. The tracking system centers close-up images on the laparoscopic target.

Introduction. Laparoscopic surgery composes a significant percentage of surgical procedures today. Arguably, the role of minimally invasive surgery (MIS) has expanded even more rapidly in the pediatric population in recent years. (te Velde E A, Bax N M, Tytgat S H, de Jong J R, Travassos D V, Kramer W L, van der Zee D C. Minimally invasive pediatric surgery: Increasing implementation in daily practice and resident's training. Surg Endosc 2008; 22:163-166). Many aspects of MIS, including image display, have been greatly improved since its introduction several decades ago. (Stellato T A. History of laparoscopic surgery. Surg Clin North Am 1992; 72:997-1002; Spaner S J, Warnock G L. A brief history of endoscopy, laparoscopy, and laparoscopic surgery. J Laparoendosc Adv Surg Tech A 1997; 7:369-73). Unlike open surgery, however, all members of the surgical team may have always had to rely on the same captured image. (Muratore C S, Ryder B A, Luks F I. Image display in endoscopic surgery. J Soc Inf Display 2007; 15:349-356). Previously explored is the possibility of offering multiple, independent images of the laparoscopic field. (Aidlen J T, Glick S, Silverman K, Silverman H F, Luks F I. Head-motion-controlled video goggles: Preliminary concept for an interactive Laparoscopic Image Display (i-LID). J Laparoendosc Adv Surg Tech A. 2009; 19:595-598; Thakkar R K, Steigman S A, Aidlen J T, Luks F I. Individualized image display improves performance in laparoscopic surgery. J Laparoendosc Adv Surg Tech A 2012; 22:1010-1013). The quality of current laparoscopic image capture and display has paved the way for this proposed innovation: high resolution of the image allows substantial electronic ("digital") zooming without pixilation or loss of detail. Thus, while the master image captures a wide-angle view of the operative field, individual digitally zoomed windows maintain sufficient resolution even when projected onto a full screen. This can offer a realistic field of view that allows operators to focus on their individual tasks simultaneously. Previous attempts have been made to establish a surgeon-controlled image display system—including head-mounted displays controlled by motion and gaze direction. (Prendergast C J, Ryder B A, Abodeely A, Muratore C S, Crawford G P, Luks F I. Surgical performance with head-mounted displays in laparoscopic surgery. J Laparoendosc Adv Surg Tech A 2009; 19 Suppl 1:S237-S240). The example implementation combines hands-free and gaze-independent tracking, intuitiveness and multi-view capability into a plug-in system that can be adapted to any MIS platform.

The potential impact of incorporating this technology into everyday surgical practice can be powerful—diminished operative time, possibly less error, and more constructive teaching for surgical trainees. (Erfanian K, Luks F I, Kurkchubasche A G, Wesselhoeft C W, Jr., Tracy T F, Jr. In-line image projection accelerates task performance in laparoscopic appendectomy. J Pediatr Surg 2003; 38:1059-1062; Peters J H, Fried G M, Swanstrom L L, Soper N J, Sillin L F, Schirmer B, Hoffman K; SAGES FLS Committee. Development and validation of a comprehensive program of education and assessment of the basic fundamentals of laparoscopic surgery. Surgery 2004; 135:21-27). The primary focus of this study was to demonstrate the feasibility of an instrument-driven individual image display.

MATERIALS AND METHODS. General surgery residents (post-graduate year, PGY, 2 through 5) were recruited to participate in this study. Residents participated in a task that has been validated by the Fundamentals of Laparoscopic Surgery (FLS®) program. The Peg Transfer task was modified here to reflect a two-surgeon approach, as previously reported. Briefly, one operator picks up a bead from a peg and hands it over to the second operator, who places it on a contralateral peg. Total time to transfer all six heads is recorded, as are the number of head drops.

Figure 9:
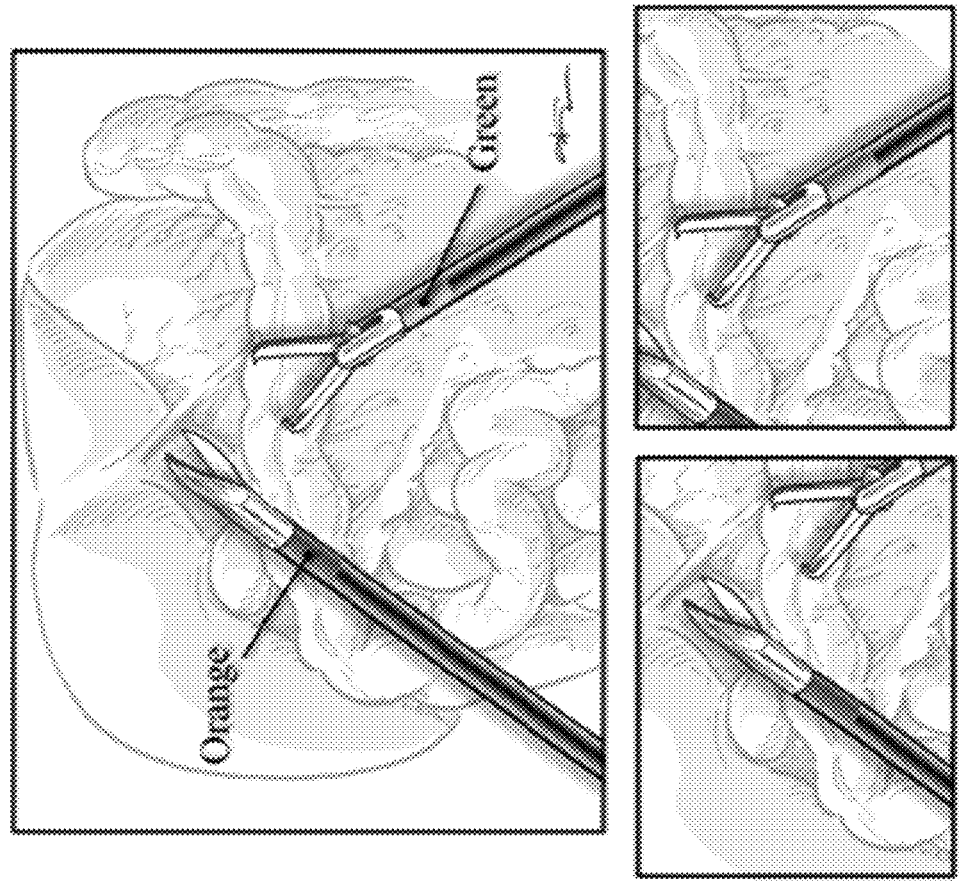
FIG. 9 is an illustration of the concept of instrument-driven Laparoscopic Image Display (iLID) navigation: the single telescope+camera captures a high-definition, wide-angle view of the operating field (top)

A software-based navigation system was designed to allow panning and zooming of two sub-windows within a "mother" image. Manipulation of each window was triggered by the recognition of a unique color reference (mounted as a ring of colored tape near the tip of an endoscopic instrument) (FIG. 9). This software prototype was written in Python™ and NumPy using OpenCV and OpenGL®, and allowed reliable independent tracking of two color markers. (Luks F I, Ha A Y, Merck D L, Fallon E A, Ciullo S S. i-LID—Instrument-driven laparoscopic image display (Abstract). Presented at the Annual Conference of the Society of American Gastrointestinal and Endoscopic Surgeons (SAGES), Apr. 2-5, 2014, Salt Lake City, UT 2014.) Image processing/display pipeline comprised of these steps: 1) Master image was collected from the video stream, 2) for each window, the camera image was thresholded for optical targets (distinct hues—orange and green in the example in FIG. 9), 3) thresholded image moments were computed, and instrument tip image position was estimated based on known instrument geometry, 4) tip position estimate was input into a Kalman filter to smooth the estimate over time, and 5) the original image was cropped and scaled for rendering in the daughter window. Cropping was about the tip of the instrument, as estimated in step 3).

FIG. 9 is an illustration 900 of the concept of instrument-driven Laparoscopic Image Display (iLID) navigation: the single telescope+camera captures a high-definition, wide-angle view of the operating field (top). Two daughter images are generated by centering the window on the respective color codes near the tip of the endoscopic instruments. The left display centers the window on the orange instrument, the right one on the green instrument.

The display router consisted of a desktop computer with high-end video processing system capable of providing simultaneous display of two daughter windows with minimal latency (defined as 50-80 ms for the purpose of in vitro testing, as this corresponds to the latency of the standard endoscopic camera system available in the operating room immediately before it was converted to high definition imaging); input capabilities for a USB camera or a standard digital charge-coupled device (CCD) camera with 10 mm 0° telescope, via SDI interface; and VGA output capabilities for display on standard video monitors.

All residents performed the tasks in Experimental mode and in at least one Control: Control 1, standard mode (immobile image captured via the FLS® USB-camera, offering a wide-angle view of the entire field, displayed via a single overhead monitor); Control 2, using a 10 mm telescope and standard CCD camera manipulated by one operator, which allowed for close-up of the task, displayed on a single overhead monitor; and Experimental group, whereby a single image capture (via the FLS® USB wide angle camera) was routed through the desktop computer, and each of two video monitors displayed the image window tracking the corresponding operator's color-coded instrument (orange or green). Each team performed the tasks during the same session, after a 5-minute "warm-up" period. The order in which the tasks were performed was assigned at random.

Rhode Island Hospital's Institutional Review Board (IRB) waived the requirements for human subject protection for these ELS® studies, as the residents are not considered subjects, and because their participation in the study did not influence their academic performance and evaluation. Statistical analysis was performed using Analysis of Variance (ANOVA) for multiple groups and Wilcoxon Signed Rank Test for post-hoc paired analysis. $P<0.05$ indicates statistical significance.

Figure 10:
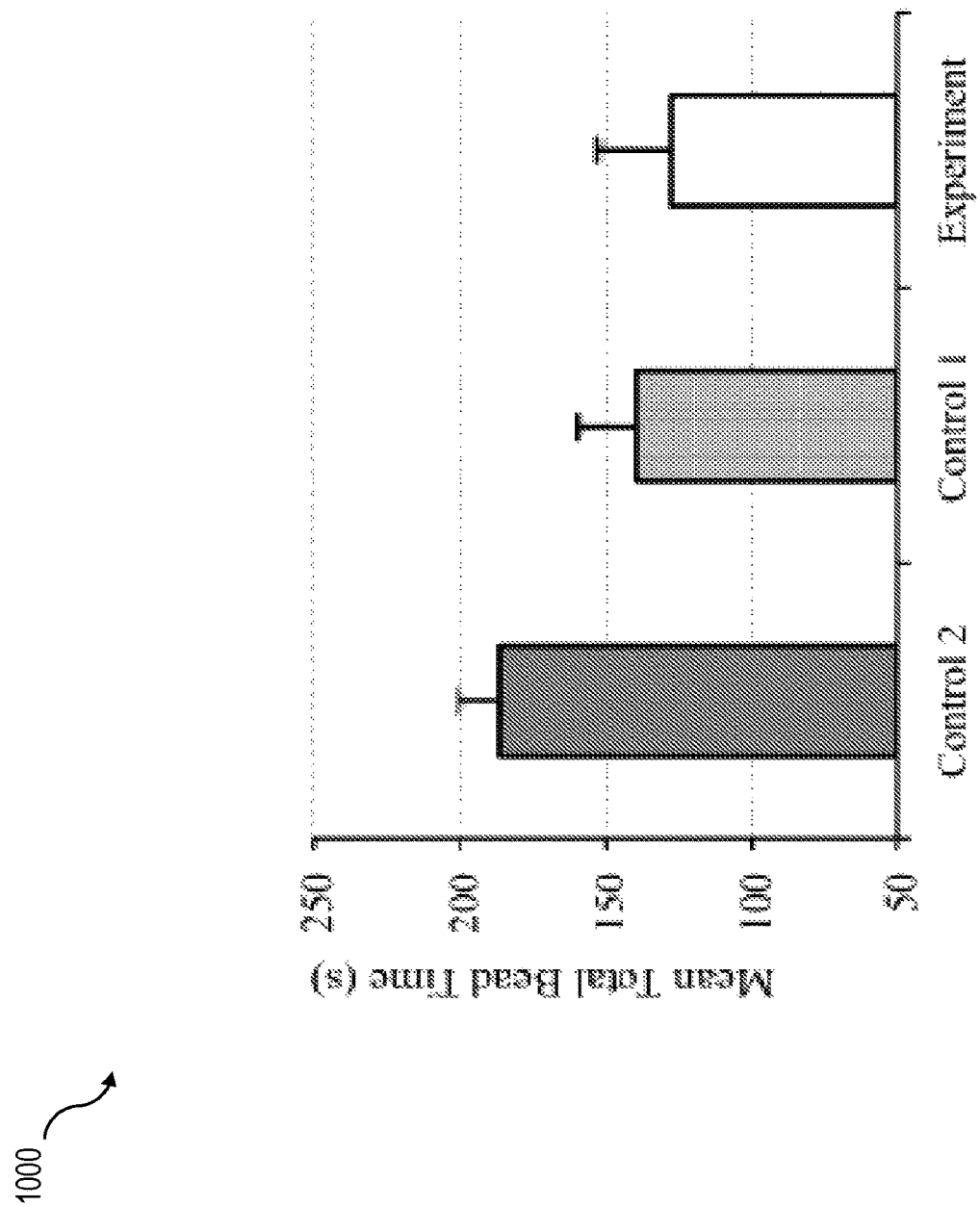
FIG. 10 is an illustration of mean total bead transfer time, in seconds, for Control 2 (single close-up endoscopic camera held by one of the two operators), Control 1 (static wide-angle FLS® camera) and Experimental groups.
Figure 11:
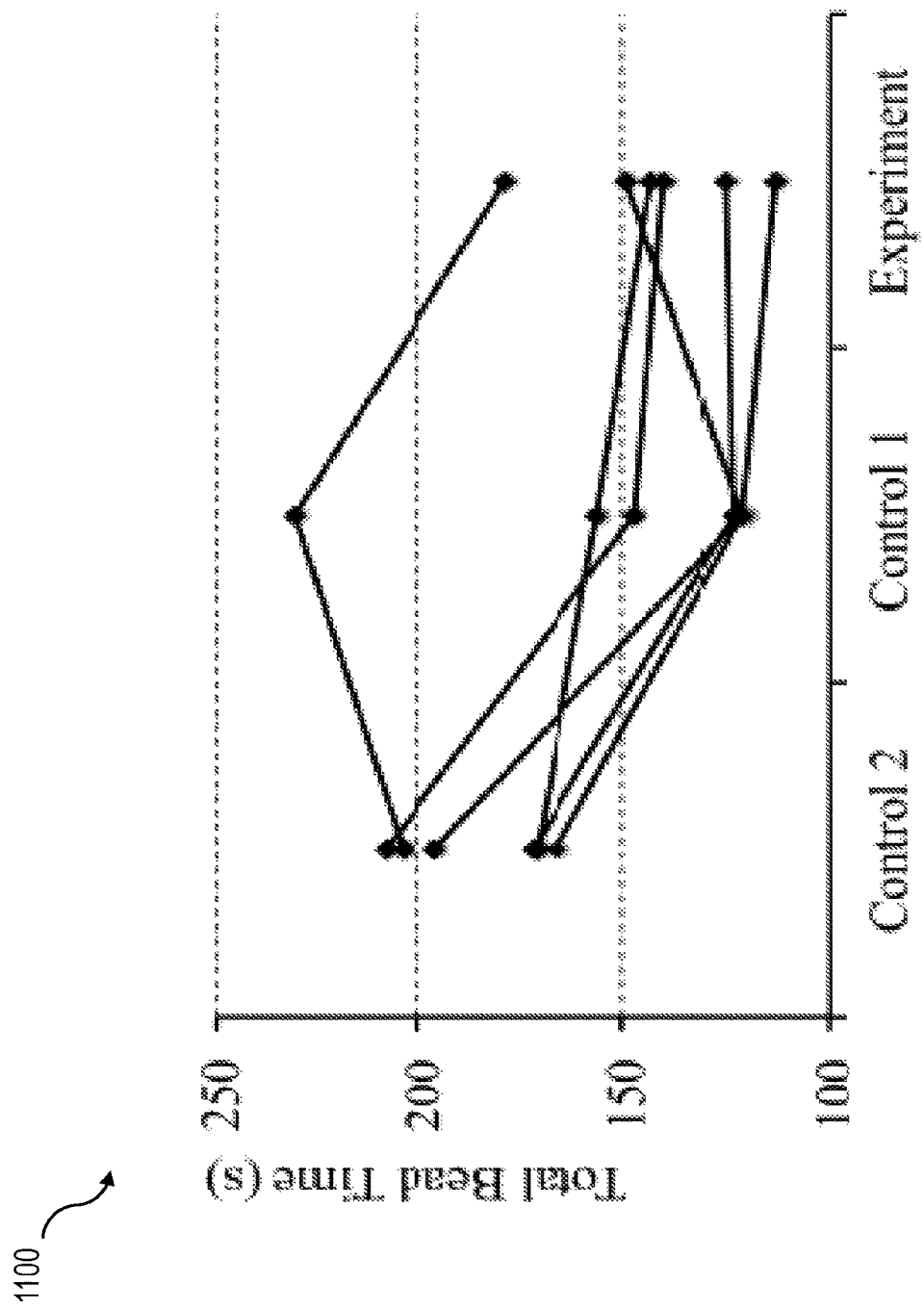
FIG. 11 is an illustration of total bead transfer times, in seconds, for those subject groups who performed all three tests.

RESULTS. Thirty-six individual sessions were performed by pairs of surgical residents in their second-through-fifth post-graduate year. Twenty-five residents participated in the study. Residents were always paired by level of experience (Post-graduate Year, PGY). Each of the 36 sessions consisted of one Experimental setting and at least one control (1 or 2). In six instances, a session consisted of Experiment and both controls—these are the subject of FIG. 10. The overall times are shown in FIG. 10. Average total time for bead transfer, expressed as mean±standard deviation (SD), was 127.3±21.3 s in the Experimental group, 139.1±27.8 s in Control 1 (single wide-angle camera) and 186.2±18.5 s in Control 2 (single hand-held, close-up telescope+camera) ($P=0.034$, Analysis of Variance, ANOVA). Paired analysis (Wilcoxon Signed Rank Test) showed that the Experimental group was significantly faster than the Control 1 group ($P=0.035$) and the Control 2 group ($P=0.028$). Intra-observer differences for those resident teams who performed in all three modes are illustrated in FIG. 11. Bead drops did not significantly differ: 0.50±0.73 beads/run in the Experimental group, compared with 0.63±0.81 in Control 1 and 0.50±0.84 in Control 2.

FIG. 10 is an illustration 1000 of mean total bead transfer time, in seconds, for Control 2 (single close-up endoscopic camera held by one of the two operators), Control 1 (static wide-angle FLS® camera) and Experimental groups (see text for details). Experimental group significantly faster than controls, ANOVA. FIG. 11 is an illustration 1100 of total bead transfer times, in seconds, for those subject groups who performed all three tests. All subjects performed better in the Experimental run than in the controls.

DISCUSSION Laparoscopic image capture and image display have undergone significant improvements throughout the more than 20 years' history of modern minimally invasive surgery. These include 3-D, high-definition (HD) and digital imaging. (King B W, Reisner L A, Pandya A K, Composto A M, Ellis R D, Klein M D. Towards an autonomous robot for camera control during laparoscopic surgery. J Laparoendosc Adv Surg Tech A 2013; 23:1027-1030; Kumar A, Wang Y Y, Wu C J, Liu K C, Wu H S. Stereoscopic visualization of laparoscope image using depth information from 3D model. Computer methods and programs in biomedicine 2014; 113:862-868.) There have even been attempts at manipulating the image as a whole, such as mirror-image and augmented reality (superimposition of pre-acquired data), or the monitors themselves (optimal position and viewing angle of the display). (Tokunaga M, Egi H, Hattori M, Suzuki T, Kawahara T, Ohdan H. Improving performance under mirror-image conditions during laparoscopic surgery using the Broadview camera system. Asian journal of endoscopic surgery 2014; 7:17-24; Wilhelm D, Reiser S, Kohn N, Witte M, Leiner U, Miihlbach L, Ruschin D, Reiner W, Feussner H. Comparative evaluation of HD 2D/3D laparoscopic monitors and benchmarking to a theoretically ideal 3D pseudodisplay: even well-experienced laparoscopists perform better with 3D. Surg Endosc 2014 Mar. 21.) However, all members of the surgical team have had to rely on the same captured image—unlike conventional open surgery, whereby all team members determine their own point of view. For that reason, laparoscopic and other MIS operations have limited surgeons in their ability to multi-task and to focus on more than one point of view at a time. This, in turn, has raised safety issues, as the inability to zoom in on the target organ while observing the periphery of the surgical field has led to tunnel vision. (Heemskerk J, Zandbergen R, Maessen J G, Greve J W, Bouvy N D. Advantages of advanced laparoscopic systems. Surg Endosc 2006; 20:730-733; Cuschieri A. Epistemology of visual imaging in endoscopic surgery. Surg Endosc 2006;20 Suppl 2:S419-24.)

With the advent of high definition (HD) image display, it is now possible to capture a wide-angle laparoscopic image and electronically zoom in on a small window without loss of detail or pixilation. The position of this window (and the degree of zoom) can be manipulated by an individual operator without altering the capture of the "master" image—and several such "daughter" images can be created and manipulated independently of each other. This concept can free laparoscopy and other MIS techniques from the single-image constraint, thereby allowing multiple points of view and multiple degrees of close-up to be displayed simultaneously. This, in turn, can allow multitasking during laparoscopy, and can compensate for suboptimal image capture (poor centering, tremor, etc.) by the telescope—often manned by the most junior and least experienced person on the surgical team.

First developed is a prototype of interactive laparoscopic image display to enable hands-free manipulation of the image via head-mounted displays (HMD). Using 3-dimensional tracking (3D mouse) based on perpendicular electromagnetic coils, the HMD interacted with the image processor to allow hands-free manipulation of the image based on spatial position and orientation of the HMD. Image manipulation used software only, allowing real-time linkage of head motion and displayed image. While HMDs epitomize image individualization and maximize hand-eye coordination by keeping the target image and the operator's instruments in the same field of vision, they have limited practical use. Immersion technology, by definition, isolates the operator from collaborators, which may impair critical communication and interaction during surgical interventions. And until robust wireless technology is available, they can tether the surgeon to the operating table, and this nuisance becomes a hazard if multiple team members are likewise tethered by cables.

Although overhead video monitors offer more environment awareness than HMDs, the simultaneous display of independently moving images could theoretically cause confusion, and be less, rather than more, efficient. Therefore studied is the feasibility and value of a multi-user multiple display system in a validated in vitro model of MIS. Two-surgeon exercises were performed with a single camera (control), and with two surgeon-controlled cameras, each generating a separate image. Showed is a significant reduction in operating time, for two different exercises, with the use of individual cameras. Moreover, the reduction in operative time was more pronounced in the expert group than in the novice group. This indicates that the device is not just a tool to help shorten the learning curve for new users. Rather, it can offer the advanced laparoscopists access to skills they were previously unable to perform—multitasking and simultaneously focusing on a close-up of the target and on a wider operative field.

The current study and implementation offers the ability to manipulate two (or more) daughter windows of the laparoscopic "master" image independently, intuitively and without the need for additional hardware or manipulators. The optimal endoscopic image centers on the tip of the instrument and the target organ—therefore, recognition software that uses the instrument tip as a trigger to manipulate the daughter image(s) automatically produces ideal image framing, and can even compensate for poor image capture. (Forgione A, Broeders I, Szold A. A novel, image based, active laparoscope manipulator—Preliminary clinical results with the Autolap system (Abstract). Presented at the Annual Conference of the Society of American Gastrointestinal and Endoscopic Surgeons (SAGES), Apr. 2-5, 2014, Salt Lake City, UT.) By expanding the possibilities and the field of view (for example, by allowing close-up and panoramic view at the same time), tunnel vision that is inherent to traditional laparoscopic visualization systems may be eliminated.

The primary goal of this research was to establish proof of concept. The new technology is intuitive enough to allow for swift adaptation during practice trials lasting no more than five minutes. Following this, the performance by residents on FLS®-standardized tasks was improved because of the enhanced multi-view capacity. In this in vitro head-passing test, the interactive image display performed better than a single, wide-angle view (traditional FLS® set-up). Residents reported better details, and overall time was significantly faster with the interactive instrument-driven image display. However, because the fixed wide-angle image (Control 1) displayed all pegs, the true benefit of multiple independent images could not be demonstrated. Therefore added is a second control group to more realistically simulate live endoscopic surgery: by allowing one surgeon to hold a telescope, the endoscopic image could zoom in on the target and offer greater detail but not follow two instruments at once. When compared with this control group, the interactive display performed far better, because it provided the same level of detail while allowing multitasking. As a result, improvement in overall bead transfer time was highly significant.

If the results of these endotrainer experiments can be replicated in a clinical situation, it would suggest that this instinctive tracking system saves operator time by optimizing efficiency. Plans are in place to expand the use of this technology to in vivo studies in order to further demonstrate the improved efficiency that it can afford to surgeons. With more dynamic and flexible zoom capacity and focus, intended to be shown is that this optimization of operator conditions not only decreases surgery time, but may increase surgical precision as well.

Another aspect of this new technology—and one that has not yet been studied—is the educational implication. The independent laparoscopic tracking is highly suitable for surgeons-in-training, whereby an attending surgeon can assume the role of "distant observer" by setting up a zoomed-out but well-focused field of view, while the trainee can independently perform the surgical task. This offers the added safety of multiple viewpoints, free from inadequate camera work.

The study design is not without its limitations. Although the FLS® tasks are standardized, reproducible and predictive of laparoscopic skills, they do not accurately simulate intra-operative visualization scenarios. The color-coding may not be as easily verified in a situation that involves multiple shades of similar colors; glare, inadequate white balance, and conflicting signals could cause temporary loss of control. In addition, the system may require sophisticated drift correction and centering mechanisms, as well as reliable zooming function algorithms. Furthermore, the system relies on a wide-angle capture of the surgical field—something that is not routinely done in clinical laparoscopy, where close-ups on the target organ and instruments are the norm. It is likely that the optimal use of the system will require re-education of the role of the cameraman, who will have to maintain a still, all-encompassing view of the entire operative field. However, minor drifts and unsteady camerawork is predicted to be cancelled out by the very nature of the new system, whereby centering of the image is based on the instrument, not the telescope.

The potential advantages of the system are substantial, however. Once mature, this device can completely free each member of the surgical team from the absolute rule of a single image—without removing any of the aspects of traditional MIS image capture and display. Because this is supplemental technology, acceptance by surgical teams may be easier. And because it is designed as a self-contained plug-and-play device between the camera output and the video monitors, it is platform-independent, and therefore adaptable to most surgical suites.

Although a few variations have been described in detail above, other modifications are possible. For example, digital post-processing can be performed using additional information relevant in laparoscopic, thoracopic, and endoscopic procedures to create enhanced and augmented views for clinical operators. The additional information can include: (1) information about the operating room and the patient, such as additional endoscopic video streams, and the 3D positions of instruments and shapes of anatomic structures; and (2) supplemental information such as 3D medical imaging (e.g., computed tomography or "CT"), procedure plans, and the like. In some implementations, given positional information about the instruments relative to the camera viewpoint, a steadycam-like effect can be created and focused on the surgical instrument and aids in keeping the instrument itself focused in the field of view.

Another example variation can include using 3D positional information from other signaling modalities such as inertial or magnetic sensor systems. Using known 3D poses of multiple cameras, their output can be stitched together, using, for example, panoramic stitching algorithms. In this case, 3D positional information can be used, which can either be determined/acquired by 3D trackers, and/or by using optical markers and multi-view geometry. Another example variation can include projecting a grid pattern onto the patient anatomy and using the pattern features to establish relative camera poses using a method such as described in Nistér, David. "An Efficient Solution to the Five-Point Relative Pose Problem." Pattern Analysis and Machine Intelligence, IEEE Transactions on 26, no. 6 (2004): 756-70. The projections can be turned off and a panorama stitched together, which can later be decomposed into an optimal view (and can be steadied against a tracked instrument).

Another example variation can include projecting relevant supplemental information (position of a target lesion, for example) into the operative space and augmenting a viewpoint by using positional information about the relative pose of supplemental imaging modalities (e.g., a previously collected 3D CT study) relative to the camera (or a synthesized viewpoint as described above).

Another example variation can include using a 3D depth map of the patient anatomy as a mediator between the camera and supplemental CT data. In this situation, a dense depth map of the intraoperative laparoscopic scene can be recovered (e.g., using laser, optical, or sonic ranging) and this surface can be registered to similar structures in the CT (e.g., the visible surface of the kidney to the segmented kidney in the CT data). The camera's position relative to the patient anatomy can be determined and relevant supplemental information can be projected into the scene to create an augmented viewpoint.

In some implementations, the current subject matter can be extremely flexible, can accept many inputs, and can support many simultaneous outputs. As the system integrates 3D data sources into the patient space, it can be used to drive advanced displays (stereo or virtual/augmented reality) and/or can be used for robotic decision making, collision prediction, and 3D navigation support.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the implementations described above can be directed to various combinations and subcombinations of the disclosed features and/or combinations and subcombinations of several further features disclosed above. In addition, the logic flows depicted in the accompanying figures and described herein do not require the particular order shown, or sequential order, to achieve desirable results. Other embodiments may be within the scope of the following claims.

What is claimed is:

1. A method comprising:
receiving data characterizing at least one mother video feed acquired by at least one endoscopic video capture device, the at least one mother video feed for characterizing an operative field within a patient;
generating, using at least one data processor and the data characterizing the at least one mother video feed, a first daughter video feed comprising a first sub-portion of the at least one mother video feed, wherein a location of the first daughter video feed within the at least one mother video feed and a zoom of the first daughter video feed is based on a first predefined marker;
generating simultaneously with generation of the first daughter video feed, using at least one data processor and the at least one mother video feed, a second daughter video feed comprising a second sub-portion of the at least one mother video feed, wherein a location of the second daughter video feed within the at least one mother video feed and a zoom of the second daughter video feed is based on a second predefined marker; and
wherein the first daughter video feed automatically pans through the at least one mother video feed by changing the location of the first daughter video feed and based on the first predefined marker;
switching a source of the first daughter video feed from the at least one mother video feed to a second mother feed based on an action associated with a surgical instrument.

2. The method of claim 1, wherein the first daughter video feed location is centered on the first predefined marker.

3. The method of claim 1, wherein the first predefined marker is located at or near a distal end of the first surgical instrument; and the second predefined marker is located at or near a distal end of the second surgical instrument.

4. The method of claim 1, wherein the endoscopic video capture device is hand-held.

5. The method of claim 1,
wherein the location of the first daughter video feed defines a sub-portion of the at least one mother video feed; and/or
wherein the zoom of the first daughter video feed defines a level of magnification and a window size.

6. The method of claim 1, wherein the zoom of the first daughter video feed is based on a present size of the first predefined marker within the at least one mother video feed.

7. The method of claim 1, further comprising displaying the first daughter video feed and the second daughter video feed separately for viewing during videoscopic procedures.

8. The method of claim 1, wherein the first sub-portion of the at least one mother video feed is a windowed portion of the at least one mother video feed.

9. The method of claim 1, wherein the location and the zoom of the first daughter video feed is independent of a position and/or a gaze of a surgeon.

10. The method of claim 1, further comprising:
generating simultaneously with generation of the first daughter video feed, using at least one data processor and the at least one mother video feed, a third daughter video feed comprising a third sub-portion of the at least one mother video feed, wherein a location of the third daughter video feed within the at least one mother video feed and a zoom of the third daughter video feed is based on a third predefined marker.

11. The method of claim 1, further comprising:
changing an orientation of the at least one mother feed based on the action associated with the surgical instrument.

12. A system comprising: at least one data processor; and memory storing instructions, which when executed by the at least one data processor, implement operations comprising:
receiving data characterizing at least one mother video feed acquired by at least one endoscopic video capture device, the at least one mother video feed for characterizing an operative field within a patient;
generating, using at least one data processor and the data characterizing the at least one mother video feed, a first daughter video feed comprising a first sub-portion of the at least one mother video feed, wherein a location of the first daughter video feed within the at least one mother video feed and a zoom of the first daughter video feed is based on a first predefined marker;
generating simultaneously with generation of the first daughter video feed, using at least one data processor and the at least one mother video feed, a second daughter video feed comprising a second sub-portion of the at least one mother video feed, wherein a location of the second daughter video feed within the at least one mother video feed and a zoom of the second daughter video feed is based on a second predefined marker;
wherein the first daughter video feed automatically pans through the at least one mother video feed by changing the location of the first daughter video feed and based on the first predefined marker;
switching a source of the first daughter video feed from the at least one mother video feed to a second mother feed based on an action associated with a surgical instrument.

13. The system of claim 12, wherein the first daughter video feed location is centered on the first predefined marker.

14. The system of claim 12, wherein the first predefined marker is located at or near a distal end of the first surgical instrument; and the second predefined marker is located at or near a distal end of the second surgical instrument.

15. The system of claim 12, wherein the endoscopic video capture device is hand-held.

16. The system of claim 12, wherein the location of the first daughter video feed defines a sub-portion of the at least one mother video feed; and/or wherein the zoom of the first daughter video feed defines a level of magnification and a window size.

17. The system of claim 12, wherein the zoom of the first daughter video feed is based on a present size of the first predefined marker within the at least one mother video feed.

18. The system of claim 12, the operations further comprising displaying the first daughter video feed and the second daughter video feed separately for viewing during videoscopic procedures.

19. The system of claim 12, wherein the first sub-portion of the at least one mother video feed is a windowed portion of the at least one mother video feed.

20. The system of claim 12, the operations further comprising:
changing an orientation of the at least one mother feed based on the action associated with the surgical instrument.

* * * * *